US006812458B2

(12) United States Patent
Gregori et al.

(10) Patent No.: US 6,812,458 B2
(45) Date of Patent: Nov. 2, 2004

(54) SYSTEMS AND METHODS FOR HIGH-THROUGHPUT MICROFLUIDIC SAMPLE ANALYSIS

(75) Inventors: Matthew M. Gregori, Pasadena, CA (US); Joseph F. Covington, San Gabriel, CA (US); Steven E. Hobbs, West Hills, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/637,234

(22) Filed: Aug. 8, 2003

(65) Prior Publication Data

US 2004/0026617 A1 Feb. 12, 2004

Related U.S. Application Data

(60) Provisional application No. 60/401,912, filed on Aug. 8, 2002.

(51) Int. Cl.[7] .............................................. H01J 49/00
(52) U.S. Cl. .................. 250/288; 250/281; 210/198.2; 210/656; 210/659
(58) Field of Search ........................... 250/288, 281, 250/282; 210/198.2, 656, 659

(56) References Cited

U.S. PATENT DOCUMENTS

| | | | | |
|---|---|---|---|---|
| 6,054,047 A | * | 4/2000 | Hindsgaul et al. | 210/198.2 |
| 6,066,848 A | | 5/2000 | Kassel et al. | 250/288 |
| 6,264,892 B1 | | 7/2001 | Kaltenbach et al. | 422/68.1 |
| 6,280,627 B1 | | 8/2001 | Kobayashi | 210/656 |
| 6,318,157 B1 | | 11/2001 | Corso et al. | 73/61.52 |
| 6,410,915 B1 | | 6/2002 | Bateman et al. | 250/288 |
| 2002/0001815 A1 | | 1/2002 | Hindsqaul et al. | 435/7.1 |
| 2002/0068366 A1 | | 6/2002 | LaDine et al. | 436/518 |
| 2002/0189947 A1 | | 12/2002 | Paul et al. | 204/461 |
| 2002/0089663 A1 | | 5/2003 | Petro et al. | 210/656 |
| 2003/0089846 A1 | | 5/2003 | Cooks et al. | 250/281 |
| 2003/0162304 A1 | | 8/2003 | Dority et al. | 436/180 |

FOREIGN PATENT DOCUMENTS

| | | |
|---|---|---|
| WO | WO 97/04297 | 2/1997 |
| WO | WO 98/09315 | 3/1998 |
| WO | WO 00/41214 | 7/2000 |
| WO | WO 02/30486 A2 | 4/2002 |
| WO | WO 02/44684 A2 | 6/2002 |

OTHER PUBLICATIONS

Figeys, Daniel, et al., *An Integrated Microfluidics–Tandem Mass Spectrometry System for Automated Protein Analysis*, "Analytical Chemistry," vol. 70, No. 8, Sep. 15, 1998, pp. 3728–3734.

Yang, Liyu, et al., *Evaluation of a Four–Channel Multiplexed Electrospray Triple Quadrupole Mass Spectrometer for the Simultaneous Validation of LC/MS/MS Methods in Four Different Preclinical Matrixes*, "Analytical Chemistry," vol. 73, No. 8, Apr. 15, 2001, pp. 1740–1747.

Abian, J., *The Coupling of Gas and Liquid Chromatography with Mass Spectrometry*, "Journal of Mass Spectrometry," 34, (1999), pp. 157–168.

"HPLC: Micro LC/MS Analysis of Biological Samples," 1998, Web document published at www.sge.com.

(List continued on next page.)

*Primary Examiner*—Kiet T. Nguyen
(74) *Attorney, Agent, or Firm*—Vincent K. Gustafson; Michael F. Labbee

(57) ABSTRACT

Systems and methods for collecting the output of multiple simultaneously operated chromatography columns and providing the outputs to a single mass spectrometer are provided. Such systems utilize predetermined lengths of microfluidic tubing that act as storage buffers for the substantially all of the output of each column, preserving all data and, because the storage buffers are microfluidic, there is minimal diffusion between sample bands and solvent and signal clarity is preserved.

10 Claims, 5 Drawing Sheets

OTHER PUBLICATIONS

Kameoka, Jun, et al., *A Polymeric Microfluidic Chip for CE/MS Determination of Small Molecules*, "Analytical Chemistry," vol. 73, No. 9, May 1, 2001, pp. 1935–1941.

Jiang, Yun, et al., *Integrated Plastic Microfluidic Devices with ESI–MS for Drug Screening and Residue Analysis*, "Analytical Chemistry," vol. 73, No. 9, May 1, 2001, pp. 2048–2053.

Zweigenbaum, Jerry, et al., *High–Throughput Bioanalytical LC/MS/MS Determination of Benzodiazepines in Human Urine: 1000 Samples per 12 hours*, "Analytical Chemistry," vol. 71, No. 13, Jul. 1, 1999, pp. 2294–2300.

SEPIAtec, Berlin, Germany, "Multi–Parallel–HPLC," Web document published at www.sepiatec.com/download/ph-plc.pdf.

Zhang, B., et al., *Microfabricated Devices for Capillary Electrophoresis–Electrospray Mass Spectrometry*, "Analytical Chemistry," vol. 71, No. 15, Aug. 1, 1999, pp. 3258–3264.

Moore, Roger E., et al., *A Microscale Electrospray Interface Incorporating a Monolithic, Poly(styrene–divinylbenzene) Support for On–Line Liquid Chromatography/Tandem Mass Spectrometry Analysis of Peptides and Proteins*, "Analytical Chemistry," vol. 70, No. 23, Dec. 1, 1998, pp. 4879–4884.

Lin, Yuehe, et al., "Microfluidic Devices on Polymer Substrates for Bioanalytical Applications," Web document published at: http://www.pnl.gov/microcats/aboutus/publications/ microchemical/Microtechpresentation.pdf Little, David, et al., "A Parallel LC–MS/MS System for High Throughput Quantification in Drug Discovery," Application Note 248, May 2000, Micromass Technologies.

Dunn, John A., et al., "A Parallel LC/MS/MS System for the High Throughput Quantification of Clinical Trial Samples. A Validation Study," Application Note, Oct. 2002, Waters/Micromass Technologies.

Liu, H., et al., A 96–Channel Microdevice for High Throughput Electrospray Ionization Mass Spectrometry (ESI/MS), Web document published at: http://www.geocities.com/ResearchTriangle/Lab/4688/ht–ms.html.

Van Pelt, Colleen K., et al., *A Four–Column Parallel Chromatography System for Isocratic or Gradient LC/MS Analyses*, "Analytical Chemistry," vol. 73, No. 3, Feb. 1, 2001, pp. 582–588.

Janiszewski, John S., et al., *A High–Capacity LC/MS System for the Bioanalysis of Samples Generated from Plate–Based Metabolic Screening*, "Analytical Chemistry," vol. 73, No. 7, Apr. 1, 2001, pp. 1495–1501.

Wagner, Knut, et al., *An Automated On–Line Multidimensional HPLC System for Protein and Peptide Mapping with Integrated Sample Preparation*, "Analytical Chemistry," vol. 74, No. 4, Feb. 15, 2002, pp. 809–820.

Xu, Rongda, et al., "Application of Parallel Liquid Chromatography/Mass Spectrometry for High Throughput Microsomal Stability Screening of Compound Libraries," American Society for Mass Spectrometry, 2002, 13, pp. 155–165.

Xu, Rongda, et al., *High–Throughput Mass–Directed Parallel Purification Incorporating a Multiplexed Single Quadrupole Mass Spectrometer*, "Analytical Chemistry," vol. 74, No. 13, Jul. 1, 2002, pp. 3055–3062.

Wachs, Timothy, et al., *Electrospray Device for Coupling Microscale Separations and Other Miniaturized Devices with Electrospray Mass Spectrometry*, "Analytical Chemistry," vol. 73, No. 3, Feb. 1, 2001, pp. 632–638.

* cited by examiner

FIG. _2

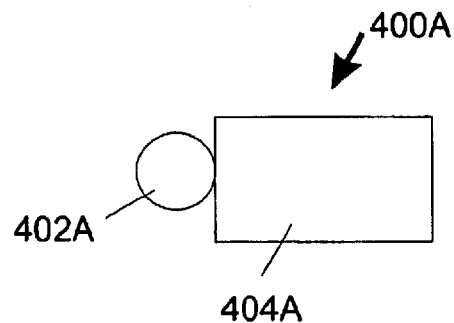
FIG. _4A
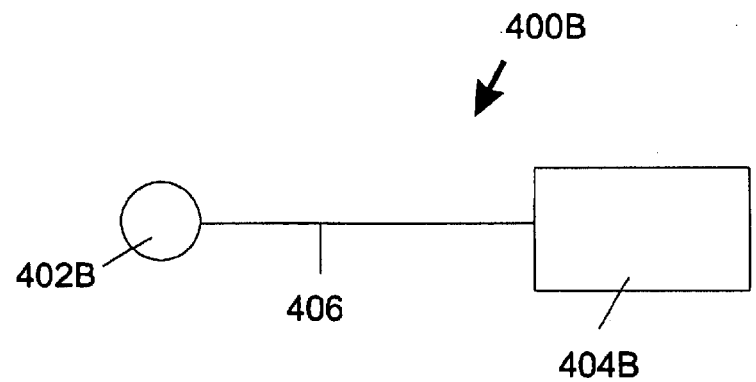
FIG. _4B
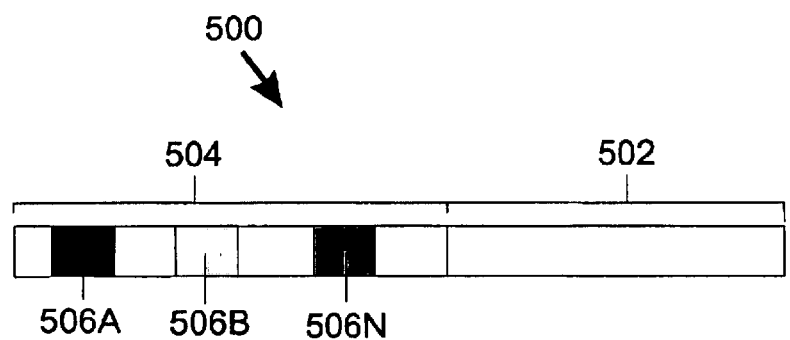
FIG. _5

SYSTEMS AND METHODS FOR HIGH-THROUGHPUT MICROFLUIDIC SAMPLE ANALYSIS

STATEMENT OF RELATED APPLICATION(S)

This application claims benefit of U.S. Patent Application No. 60/401,912 filed Aug. 8, 2002 and currently pending.

FIELD OF THE INVENTION

The present invention relates to high-throughput systems for analyzing samples by both liquid chromatography and mass spectrometry.

BACKGROUND OF THE INVENTION

Mass spectrometry (MS) is an important analysis technique in many industrial and academic fields. MS exploits the behavior of the gas-phase ions (i.e., gaseous molecules with a non-zero charge) of a molecule in response to applied electric and magnetic fields in order to deduce the composition of the molecule. The ionization process breaks a molecule into its components, the mass of each of which is then determined by analyzing the trajectory of the components as they travel through the mass spectrometer. Knowing the mass and composition of a desired molecule is especially important for pharmaceutical research, particularly in the synthesis of novel and uncharacterized molecules.

The ability to identify molecules using MS complements another analytical technique, high performance liquid chromatography (HPLC). HPLC is a physical method of separation involving sample dissolved in one or more solvents (or a "mobile phase"), wherein the solution is forced through a separation medium, typically a column packed with a fine particulate matter (or a "stationary phase"). The stationary phase, through chemical affinities, friction and/or hydrodynamic effects, acts to separate the compound (typically a complex mixture of molecules of varying size and mass) into its individual components or species. Following separation in a HPLC column, the output stream contains a series of regions having an elevated concentration of an individual component or "species" of the sample. Each of these regions appear on a chromatogram as a concentration "peak," and sometimes even comprise visible bands within the output stream. Thus, HPLC acts to provide relatively pure and discrete samples of each of the components of a compound. However, it is difficult to identify or characterize individual components using only HPLC, particularly when novel or previously uncharacterized compounds are used.

By coupling the output of an HPLC system to a MS system, it becomes possible to accurately identify and characterize each band, i.e., the component molecules of a compound. Although several techniques may be used to introduce the output of an HPLC apparatus into a MS instrument, one prevalent technique is to use an electrospray (ES) interface. ES is a "soft" ionization technique. That is, ES does not rely on extremely high temperatures or extremely high voltages to accomplish ionization, which is advantageous for the analysis of large, complex molecules that tend to decompose under harsh conditions. ES uses the combination of an applied electric field and compressed gas to generate charged droplets of the sample solution. The application of drying gases in conjunction with a vacuum causes the droplets to grow increasingly smaller until a desolvated, charged sample molecule is produced.

Recent advances in chromatography have resulted in the development of high throughput liquid chromatography (HTLC), which employs improved chromatographic columns to dramatically reduce the amount of time needed to perform high-resolution separations. Also, demand for increased throughput capacity has led to the development of multiplexed chromatography systems, which include multiple separation columns to permit the separation of multiple chemical mixtures in parallel.

Typically, a single MS instrument has a single ES component (or other suitable ionization/input device) and, as such, may only accommodate the output of a single HPLC column. Moreover, ES/MS instruments are extremely complex and expensive to operate and maintain. Thus, it would be advantageous to have the ability to couple a multiplexed HTLC system to a single ES/MS instrument, thereby minimizing the number of ES/MS systems required to analyze multiple output streams. Several systems for multiplexing multiple separation columns into a single ES/MS system have been proposed. For example, U.S. Pat. No. 6,410,915 to Bateman et al.; U.S. Pat. No. 6,191,418 to Hindsgaul et al.; U.S. Pat. No. 6,066,848 to Kassel et al.; and U.S. Pat. No. 5,872,010 to Karger et al. each show some variation of a multiplexed HPLC/MS system where the outputs of multiple simultaneously-operated separation columns are periodically sampled by a single MS device. However, in such real-time multiplexed HPLC/MS systems, only one separation column output stream can be sampled at a given time. While one stream is being analyzed, the others must continue to flow, as these systems have no storage capacity. This inherently results in data loss. To mitigate this data loss, sampling must occur very quickly. The MS instrument thus receives very small plugs of sample, reducing the ability of the instrument to integrate data in order to eliminate noise. Signal clarity, in turn, suffers.

Optical detection devices, such as UV-Visible spectrum detectors that are capable of collecting data in parallel, may be used to selectively control the sampling of multiple separation column output streams so that a region of interest in a particular stream may be sampled more frequently, thereby ameliorating the limitations of a sampling system. However, if two or more regions of interest coincide in time, which frequently occurs, such pre-screening-based sample selection will be of limited value.

U.S. Pat. No. 6,318,157 to Corso et al. ("Corso") describes a multiplexed HPLC/MS device where gradient separations are performed by staggering the initiation, of separations in four separate columns by using input lines of varying length. In this manner, each output stream may be analyzed continuously by the MS instrument. The staggering technique taught by Corso effectively acts as four serial separations. While some efficiencies are gained by not having to prepare a single column four times, the overall run time of the four columns run in a stagger is much longer than the run time of four columns run simultaneously. Also, this system incorporates numerous rotary valves that may create dead volumes and induce error. Moreover, the necessary amount of stagger (i.e., the length of each input line) must be calculated in advance to insure that regions of interest have no temporal overlap, which may be difficult when characterizing unknown compounds. Corso also suggests that the staggering of inputs is not necessary for isocratic separations; however, Corso does not indicate how overlap of regions of interest can be avoided. Presumably, a sampling technique is used, thus creating the same data loss and signal clarity issues discussed above.

Accordingly, there exists a need for a multiplexed HPLC/MS system that permits the substantially continuous analysis of the output streams of multiple simultaneously-operated separation columns with minimal loss of data and/or signal clarity.

BRIEF DESCRIPTION OF THE DRAWINGS

FIG. 4A is a schematic of an experimental system used to measure performance characteristics of a fluid injector.

FIG. 4B is a schematic of an experimental system used to measure performance characteristics of a fluid injector used in combination with a storage line.

FIG. 5 is a block diagram illustrating the components of an output stream produced by a separation column.

DETAILED DESCRIPTION OF PREFERRED EMBODIMENTS OF THE INVENTION

Definitions

The terms "column" or "separation column" as used herein are used interchangeably and refer to a region of a fluidic device that contains stationary phase material and is adapted to perform a separation process.

The term "microfluidic" as used herein refers to structures or devices through which one or more fluids are capable of being passed or directed and having at least one dimension less than about 500 microns.

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "storage line" as used herein refers to any structure adapted to convey and store a fluid while maintaining the integrity of an output stream of a separation column, including, but not limited to tubes, conduits, and channels.

Preferred Embodiments

Systems according to the present invention collect the output streams from multiple microfluidic HPLC columns and provide the streams to a smaller number of mass spectrometer(s) (MS). Such systems utilize predetermined lengths of microfluidic tubing or conduits that act as storage buffers for the output of each column. Because the entire output of each column may be stored, substantially all the output streams may be preserved. Because the storage buffers are microfluidic, there is minimal diffusion between sample bands and solvent and signal clarity is preserved.

Figure 1:
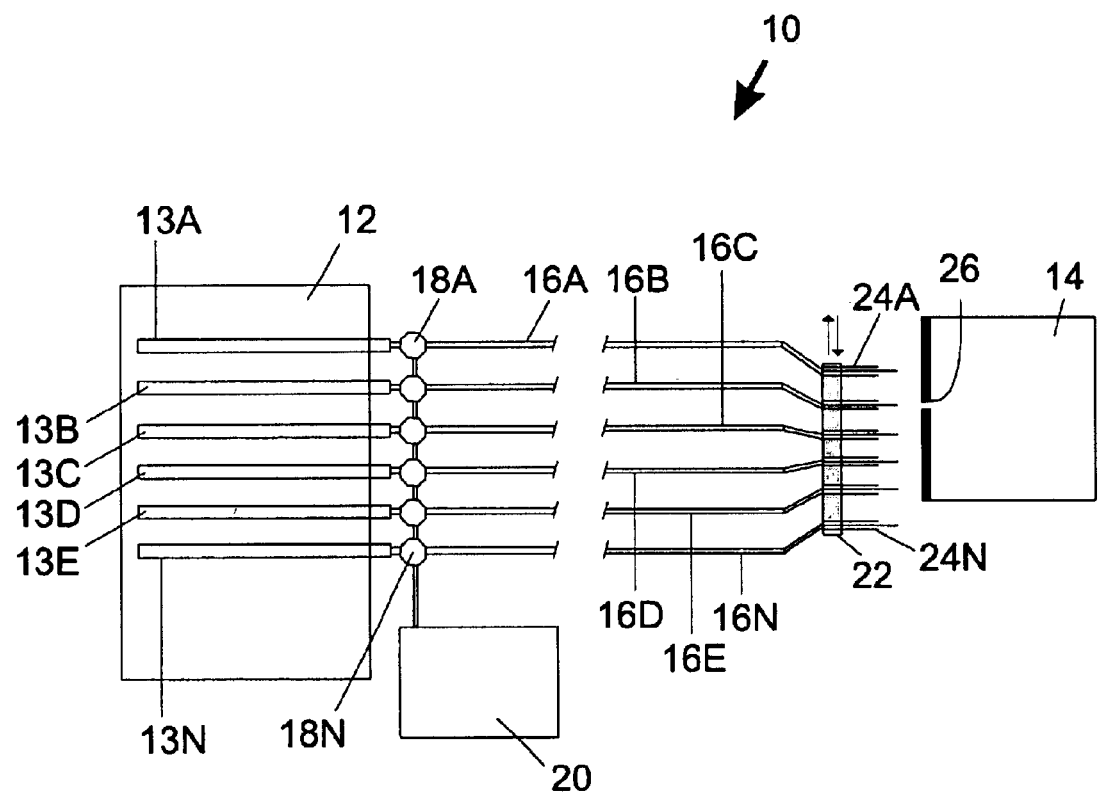
FIG. 1 is a top diagrammatic view of one embodiment of a fluid handling system for multiplexed HPLC/MS analysis according to the present invention.

Referring to FIG. 1, a HPLC/MS fluid handling system 10 according to the present invention includes a microfluidic parallel HPLC apparatus 12 having six separation columns 13A–13N (i.e., six "channels"), a microfluidic storage line 16A–16N connected to each column 13A–13N and leading to a mass spectrometer 14. (Although FIG. 1 shows the system 10 having six channels 13A–13N and six microfluidic storage lines 16A–16N, it will be readily apparent to one skilled in the art that any number of channels 13A–13N and microfluidic storage lines 16A–16N may be provided. For this reason, the designation "N" is used to represent the last channel 13N and microfluidic storage line 16N, with the understanding that "N" represents a variable and could represent any desired number of microfluidic storage lines. This convention is used throughout this document.)

The HPLC apparatus 12 may be any suitable device that includes multiple parallel separation columns 13A–13N. The columns 13A–13N may be integrated in a single chip 12; multiple independent columns (not shown); multiple independent columns positioned within a single device (not shown); or any other suitable configuration. The HPLC system 12 and its component columns 13A–13N may be manufactured by any suitable method, such as through the use of stainless steel, polymeric, or glass capillary tubes, laminated stencil layers, or by processing various materials using conventional processing techniques such as micromachining, etching or molding. The stationary phase material included in the columns 13A–13N may be selected to provide the desired performance characteristics. It will be readily understood by one skilled in the art that any form or configuration of HPLC columns may be used, the appropriate column, fabrication method and stationary phase material being selected to match the performance characteristics required for the particular separation(s). Representative parallel HPLC column devices and fabrication methods are provided in co-pending and commonly assigned U.S. patent application Ser. No. 10/638,258 entitled "Multi-Column Separation Devices and Methods" filed Aug. 7, 2003, the disclosure of which is hereby incorporated by reference as if fully set forth herein.

The system 10 also includes valves 18A–18N (numbering for valves 18B–18E is omitted for clarity) interposed between each separation column 13A–13N and its respective storage line 16A–16N. A fluid/pressure source 20 connects to the valves 20A–20N. Each of the storage lines 16A–16N connect to an associated electrospray needle 24A–24N (numbering for needles 24B–24E is omitted for clarity) and the positioning of the needles 24A–24N relative to the mass spectrometer 14 is controlled with a translation stage 22, which may have two or more degrees of freedom. The mass spectrometer 14 may be any suitable MS device selected by one skilled in the art, including, but not limited to quadrupole, tandem, triple quadrupole, ion trap, or time-of-flight mass spectrometers. It will be readily apparent to one skilled in the art that, in addition to or as an alternative to mass spectrometers, other analytical tools may be used in conjunction with fluid handling systems according to the present invention.

In operation, the desired HPLC separations are performed simultaneously in columns 13A–13N. The output stream from each column 13A–13N is directed into its associated storage line 16A–16N. Referring to FIG. 5, it should be understood that the output stream 500 from an HPLC column includes a waste segment 502 and a species segment 504. The waste segment 502 comprises the mobile phase that is forced through the column to wet the stationary phase to prepare it for the separation operation. The species segment 504 comprises mobile phase combined with the sample, which, after passage through the column, has been separated into its component species 506A–506N. The waste segment 502 of the output stream may be discarded, as it typically contains no materials of interest.

Referring again to FIG. 1, the storage lines 16A–16N are filled simultaneously. The waste segment of the output stream may be discarded before entering the storage lines or may travel through the storage lines before being diverted to a waste collector (not shown). The length of each storage line 16A–16N is selected to accommodate the species segment of mobile phase output for a single chromatographic separation on its respective column 13A–13N. Thus, if the volume of the species segment of the mobile phase output of a separation is X microliters, the volume (V) of the storage line (V=$\pi(0.5 \times ID)^2 \times L$, where ID is the inner diameter of the storage line and L is the length of the storage line) should be greater than or equal to X microliters. For example, a species segment having a volume of about 0.003 fl. oz. (about 100 microliters) requires an associated storage line 16A–16N having a length of approximately twenty-five feet (about seven and six tenth meters), assuming the internal diameter of the storage line 16A–16N is approximately five mils (about 130 microns).

Because all the separations may be run simultaneously, once the separations are complete and the species segments are stored in the storage lines 16A–16N, the valves 18A–18N may be closed and the device 12 may be prepared for the next run while the stored species segments are analyzed. However, storing the species segments for long periods of time (e.g., many minutes) may be of concern as diffusion between the separated bands of analyte and the solvent may occur. Such diffusion could cause band broadening, thereby affecting the signal clarity of the sample as it is analyzed by the mass spectrometer. It has been found that maintaining microfluidic dimensions in the storage lines 16A–16N minimizes the size of the diffusion interface between bands and solvents, thereby mitigating band broadening. Moreover, it has been found that such diffusion produces a very small contribution to total band broadening compared to other features of the system (e.g., fluid interconnections, valves, frits, etc.). As a result, there is considerable flexibility in the size of capillary tubing required to produce sufficient system performance.

Another concern is the degree of band broadening caused by the travel of the output stream through the entire length of the storage line. Band broadening in this context may be characterized by a band broadening factor (BF), which equals the ratio of peak width after passing through a storage line ("final peak width" or $W_x$) to peak width measured at the injector ("injector peak width" or $W_o$), (i.e., BF=$W_x/W_o$). Thus, if a one minute peak traveling through a seven meter storage line were to broaden to two minutes, the band broadening factor would be two (BF=2 min./1 min.=2). Another method for characterizing the band broadening is to determine the absolute or additive broadening (AB) factor, which is equal to the difference between the final peak width minus the injector peak width (i.e., AB=$W_x - W_o$). While both measures are useful, it has been found that the band broadening caused by travel through storage lines appears to be fixed or constant and not linear or geometric. Thus, in a storage line where a one-minute band is broadened to two minutes upon exiting the line, a two-minute band also is like to broaden by one minute. Accordingly, the additive broadening factor may be a more desirable measure of storage line performance.

Referring to FIGS. 4A and 4B, an experiment was conducted using a test system 400A, in which a reference analyte was provided from an injector 402A directly into an ultraviolet (UV) detector 404A. The same reference analyte was then introduced by an injector 402B into a storage line 406 and then to a UV detector 404B located at the terminus of the, storage line 406. The reference analyte was a 0.5 microliter plug of caffeine (2 milligrams/milliliter) introduced into a solvent flowing at 5 microliters/min. Table 1 shows the results of a comparison between storage lines fabricated with polyetheretherketone (PEEK) and stainless steel. Both experiments were performed using twenty-five foot (7.6 meter) storage lines with inner diameters of five mils (130 microns). Table 2 show the results of a similar experiment comparing the performance of PEEK storage lines having inner diameters of five and seven mils (130 and 180 microns, respectively) and lengths of twenty five feet (7.6 meters) and thirteen feet (four meters), respectively.

TABLE 1

Comparison of PEEK and Stainless Steel Storage Lines

| Material | W(x) (min) | W(o) (min) | BF | AB (min) |
|---|---|---|---|---|
| PEEK (5 mil) | 0.393 | 0.118 | 3.33 | 0.275 |
| SS (5 mil) | 0.604 | 0.118 | 5.12 | 0.486 |

TABLE 2

Comparison of Different Inner Diameters of PEEK Storage Lines

| ID (mil) | W(x) (min) | W(o) (min) | BF | AB (min) |
|---|---|---|---|---|
| 5 | 0.393 | 0.118 | 3.33 | 0.275 |
| 7 | 0.684 | 0.118 | 5.80 | 0.566 |

These experiments demonstrate that band broadening may be controlled by selecting the size/geometry and material properties of the storage lines 16A–16N. Thus, band broadening may be minimized by reducing the interior diameter of the storage lines 16A–16N and/or using a more hydrophobic material, such as PEEK. These parameters may be varied to tailor the system to the desired results. For example, wider or larger diameter storage lines may be used to accelerate processing where band resolution is not critical. Likewise, where band resolution is paramount, very narrow or smaller diameter storage lines may be used to minimize diffusion and broadening. Also, other materials, such as, but not limited to, polytetrafluoro-ethylene (PTFE), may be selected to further minimize or otherwise manipulate the behavior of the output stream in the storage lines 16A–16N. Suitable materials will be readily apparent to one skilled in the art.

When the separation is complete and all of the storage lines 16A–16N are filled, the fluid flow to the storage lines 16A–16N from the separation columns 13A–13N is terminated. The flow may be terminated at the pressure source driving the separation (not shown) or by the actuation of the valves 18A–18N. The valves 18A–18N may then be selectively activated to direct pressurized fluid from fluid/pressure source 20 into each storage lines 16A–16N to drive the stored fluid into the mass spectrometer 14. The valves 18A–18N are preferably actuated sequentially, allowing the entire contents of each storage line 16A–16N to be analyzed by the mass spectrometer 14 before the next storage line 16A–16N is selected.

Each storage line 16A–16N may be coupled with a dedicated electrospray needle 24A–24N in order to deliver analyte from the storage line 16A–16N to the mass spectrometer 14. The electrospray needles 24A–24N are preferably fabricated in a closely spaced array positioned in front of the mass spectrometer inlet orifice 26. When a particular output stream is to be analyzed, the needle 24A–24N corresponding to the selected storage line 16A–16N is positioned in front of the orifice 26 by the translation stage 22. The fluid flow is actuated at the upstream end of the storage line 16A–16N by actuating a, valve 18A–18N to provide pressurized fluid from fluid/pressure source 20 to the storage line 16A–16N. To analyze another sample, the translation stage 22 is repositioned and the flow actuated for the next corresponding storage line 16A–16N. This interface has the advantage of fewer connections that could cause band broadening.

Figure 2:
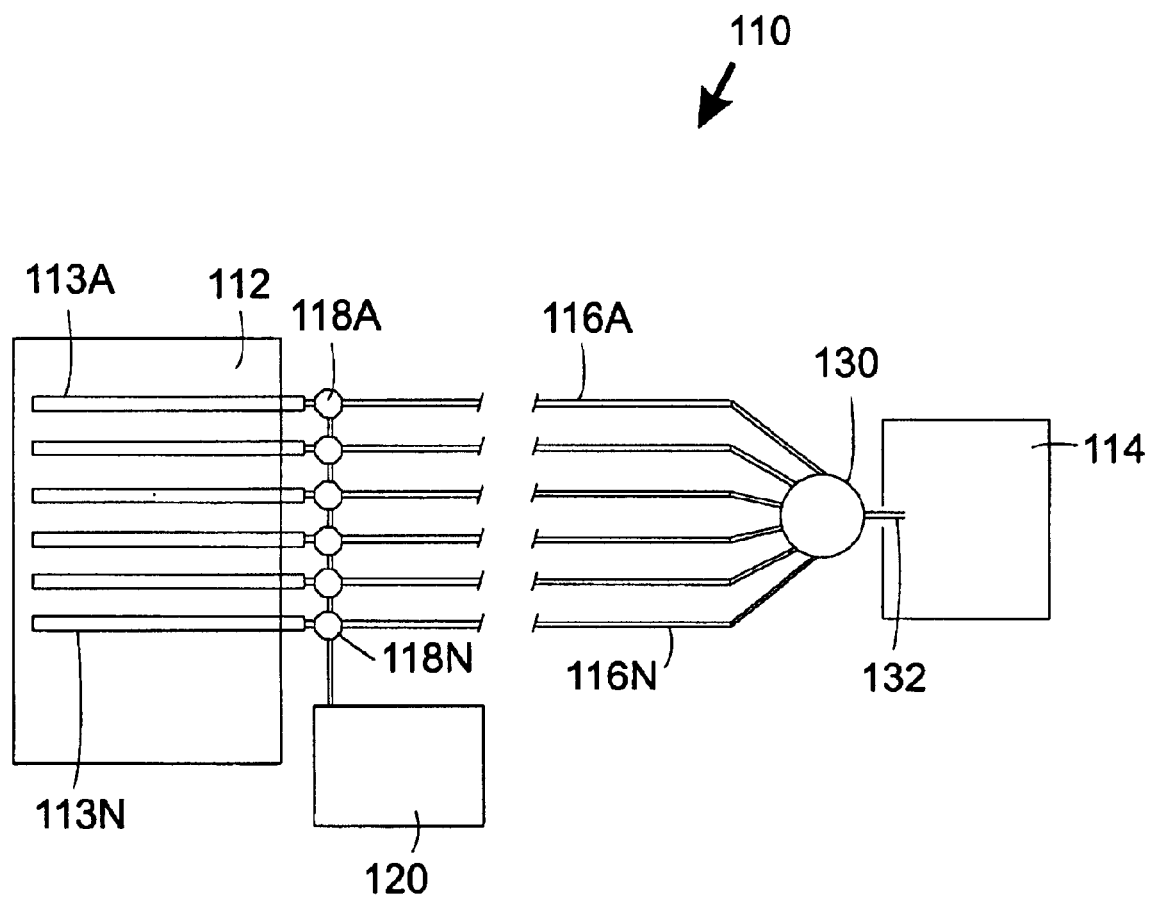
FIG. 2 is a top diagrammatic view of another embodiment of a fluid handling system for multiplexed HPLC/MS analysis according to the present invention.

In an alternative embodiment, shown in FIG. 2, system 110 is similar to the system 10 shown in FIG. 1, except that the storage lines 116A–116N are connected to the inputs of a multi-port switching rotary valve 130 (such as those produced by Valco Instrument Co. Inc, "VICI," Houston, Tex.). The single output 132 of the rotary valve 130 is linked directly to the standard input interface of the mass spectrometer 114. The rotary valve 132 is actuated to the desired storage line 116A–116N to the mass spectrometer 114. The interface shown in FIG. 2 has the advantage of requiring little or no modification of existing ES/MS interfaces and, thus, would be readily adapted to almost any commercially available ES/MS. The rotary valve 132, however, may include a dead volume that could result in undesirable band broadening. Other multi-port valves (not shown), such as translational multi-port switching valves, also may be used.

In addition, any suitable interface between the storage lines and the mass spectrometer may be used. For example, with the benefit of the present disclosure, any of the sampling interfaces described in U.S. Pat. No. 6,410,915 to Bateman et al.; U.S. Pat. No. 6,191,418 to Hindsgaul et al.; U.S. Pat. No. 6,066,848 to Kassel et al.; and U.S. Pat. No. 5,872,010 to Karger et al. could be modified to provide a switching, rather than a sampling, function and thus used in conjunction with storage lines.

Figure 3:
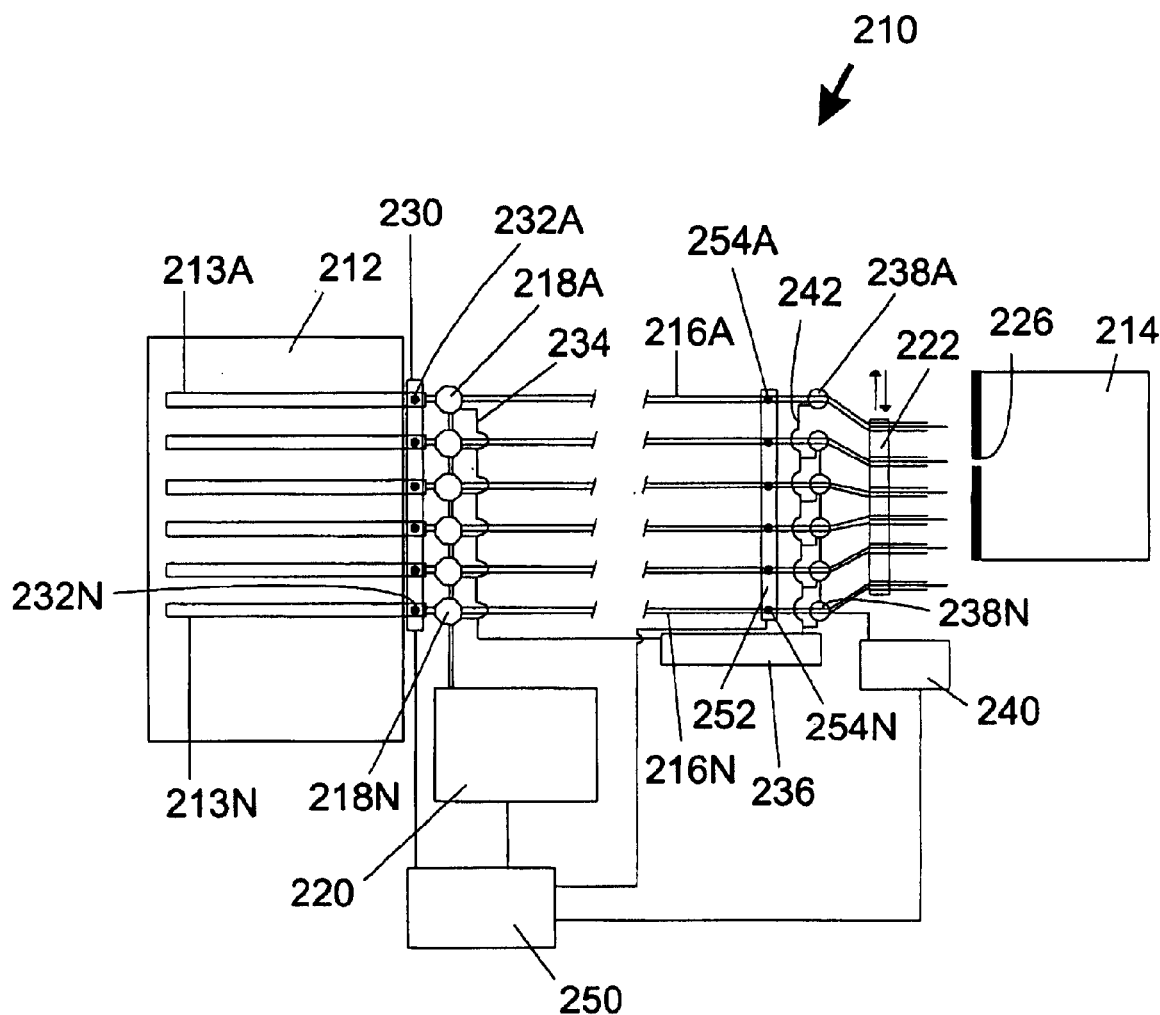
FIG. 3 is a top diagrammatic view of another embodiment of a fluid handling system for multiplexed HPLC/MS analysis according to the present invention.

In another preferred embodiment, shown in FIG. 3, a HPLC/MS system 210 also may include a pre-screening sensor array 230 in communication with a detector 250. The pre-screening detector array 230 includes sensors 232A–232N and may sense any desirable or useful characteristic of the output of columns 213A–213N such as transmissive or reflective response to ultraviolet (UV) or visible light. The detector 250 may be used to analyze the sensor data, identify compounds or regions of interest in the output streams, and/or provide data to control the analysis of the output streams. For example, if a chromatogram produced by the detector 250 indicates large separation of bands (i.e., good resolution) the mass spectrometer analysis may be performed more quickly without concerns of data loss. If, in contrast, a chromatogram produced by the detector 250 shows tightly spaced bands, the mass spectrometer analysis can be performed much more slowly in order to generate greater data resolution. Also, the detector 250 may be used to identify the waste and species segments of the output stream to control the diversion of the stream to a waste collector.

Similarly, such a feedback system may be used to vary the flow rate of a particular sample to provide high resolution during signal analysis and higher speed between signals. In other words, data from the detector 250 could be used to accelerate the flow from the storage lines 216A–216N into the mass spectrometer 214 between bands and decelerate the flow rate when the bands are being introduced into the mass spectrometer 214.

It may be desirable to position a sensor array 252 proximate to the interface between the storage lines 216A–216N and the mass spectrometer 214 to allow for more accurate control of the flow rate vis-à-vis the output stream characteristics. Alternatively, sensor arrays 230, 252 may be used at either end of the storage lines 216A–216N to provide even more control.

Thus, it may be desirable to control the flow rate of fluid from the storage lines 216A–216N to the mass spectrometer 214 to accomplish one or more desired results. For example, the output flow rate may be varied to optimize signal resolution as described above. Alternatively, the output flow rate may be accelerated for each storage line 216A–216N uniformly to accelerate overall processing times. In one embodiment, if six separation columns are used, the flow rate from the storage lines 216A–216N may be adjusted so that the time to output fluid from one of the storage lines 216A–216N into the mass spectrometer 214 has a duration of one sixth of the duration of the separation. In this manner, the entire output of all the columns 213A–213N may be analyzed in the time required to perform all of the separations.

Of course, the rate at which the samples are output from the storage lines 216A–216N may affect the quality of the data as a consequence of fluid flow effects on the samples (e.g., a high flow rate may induce turbulence thereby causing band widening or loss of resolution). Thus, it may be desirable to alter the flow rate in a manner more suited to the desired output resolution. For example, multiple mass spectrometers may be used to allow a slower output flow rate. In the embodiment described above, the use of two mass spectrometers would allow the output of the six storage lines 216A–216N two be divided into two sets of three. The mass spectrometry analysis could then performed in the same amount of time, but only requiring increasing the output flow rate by a factor of three, rather than six. This approach may be used for any number of columns and flow rates. A device incorporating sixteen, twenty-four or more separation columns could be coupled with two, four, eight or more mass spectrometers to allow for the desired output flow rate, but still minimizing the total number of mass spectrometers required to perform the desired analysis. One skilled in the art will readily recognize that any and all of the approaches described above may be combined in any number of ways to achieve the desired system performance and data resolution.

In addition, output signals from the detector 250 may be used to control valves 218A–218N and re-direct a portion of each output flow stream through sample diversion lines 234 to a fraction collector 236. In this manner, discrete samples of interest may be collected and stored for other forms of analysis. Alternatively, or in addition, valves 238A–238N may be positioned proximate to the interface between the storage lines 216A–216N in order to divert portions of the output streams through diversion lines 242 into a fraction collector 236 for the reasons noted above. The sensor array 252 may be used to provide data to the detector 250 to control the operation of the valves 238A–238N, accordingly.

Storage systems according to the invention allow entire output streams to be isolated and stored for individual analysis. This approach has several advantages over real-time sampling systems, including the negation of the data loss, improved signal resolution and the ability to simultaneously perform the MS analysis and flush and prepare the separation columns for subsequent separations. In addition, the rotary valve HPLC/MS coupling system eliminates the need to modify the ES/MS interface of existing ES/MS devices, thus allowing the system to be adapted to almost any commercially available ES/MS. The arrayed ES coupling method utilizes a much more limited range of motion. This, in combination with the ability to store the output streams for an extended period of time, allows the array to be positioned more easily and accurately than a rapidly cycling sampling system because the array is not required to move with immense speed. This increase in accuracy as well as the improvement of signal clarity and negation of data loss offsets the potential need to modify the ES/MS interface to accommodate the array.

Figure 6:
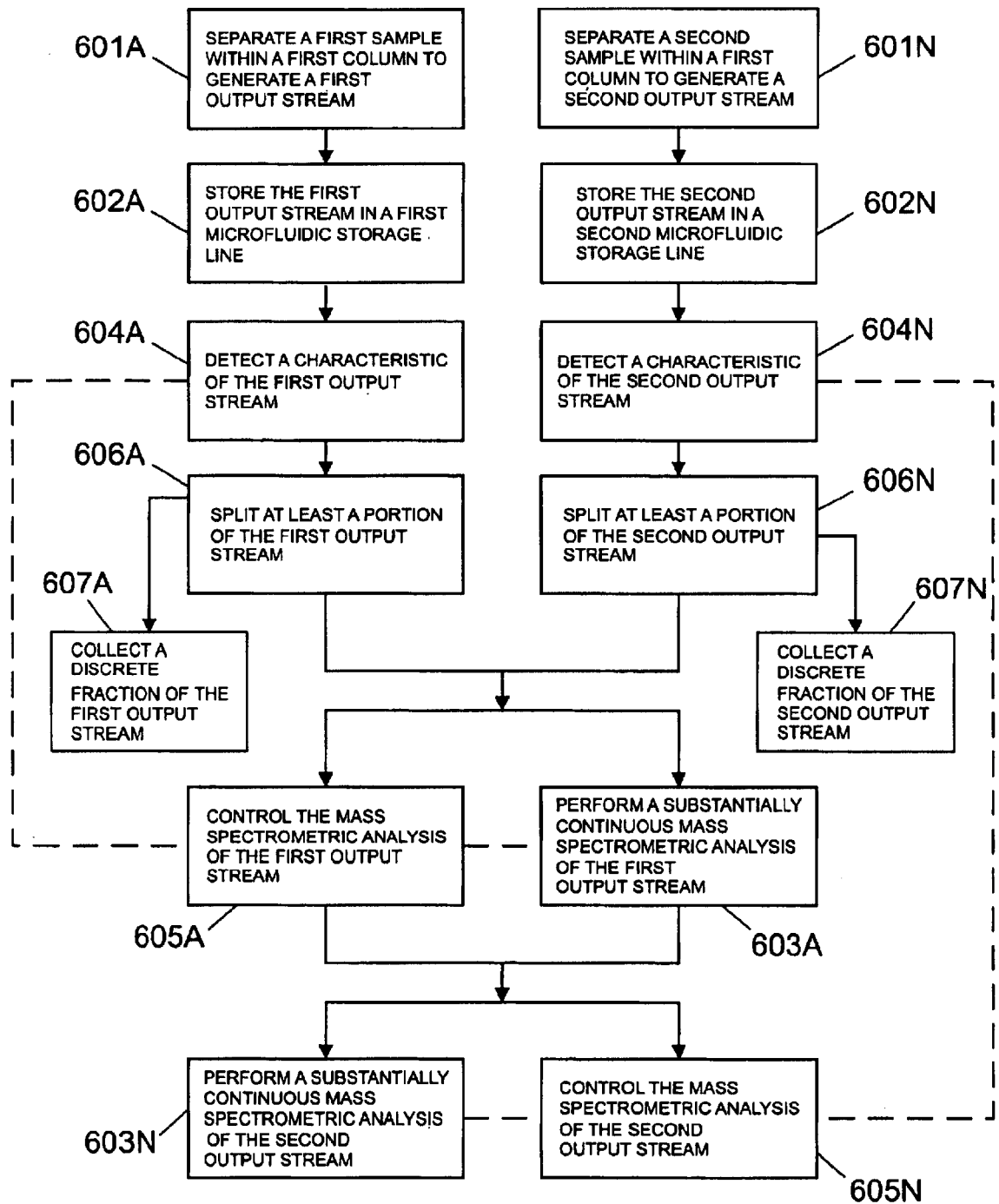
FIG. 6 is a flowchart of a method for operating a multi-column liquid chromatography apparatus with storage lines coupled to a mass spectrometer.

A flowchart outlining the steps of a method for operating a multi-column liquid chromatography apparatus with storage lines coupled to a mass spectrometer is provided in FIG. 6. A first step 601A includes separating the first sample within a first separation column to generate a first output stream. A second step 602A includes storing the first output stream in a first microfluidic storage line. A third step, 601N, which occurs substantially simultaneously to the first step 601A, includes separating a second sample within a second separation column to generate a second output stream. A fourth step 602N, which occurs substantially simultaneously to the second step 602A, includes storing the second output stream in a second microfluidic storage line. A fifth step 603A includes performing a substantially continuous mass spectrometric analysis of the contents of the first output stream. A sixth step, which occurs substantially simultaneously to the fifth step 603A, includes performing a substantially continuous mass spectrometric analysis of the contents of the second output stream. (Note that while FIG. 6 illustrates operation of a system with only two parallel sample separation columns and microfluidic storage lines, it will be readily understood by one skilled in the art that any number of columns and storage lines may be used.)

Optional steps include detecting a characteristic of the first and/or second output streams 604A, 604N and controlling the mass spectrometric analysis in accordance with the detected characteristics 605A, 605N (as described above). For example, the flow rate of the output streams into the mass spectrometer may be varied based on the presence or absence of species of interest. Optional steps also include splitting the output streams 606A, 606N so that a portion of each may be collected in a fraction collector 607A, 607N.

A wide variety of samples may be used with methods and systems according to the present invention. Preferably, any of the method steps may be automated. Automation means preferably include a programmable microprocessor such as contained within a personal computer or other conventional processing device.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A method for analyzing a first sample and a second sample, the method comprising the steps of:
    a) separating the first sample within a first separation column to generate a first output stream;
    b) substantially simultaneously with step a), separating the second sample within a second separation column to generate a second output stream;
    c) storing the first output stream in a first microfluidic storage line;
    d) substantially simultaneously with step c), storing the first output stream in a second microfluidic storage line;
    e) performing a substantially continuous mass spectrometric analysis of the contents of the stored first output stream; and
    f) subsequent to step e), performing a substantially continuous mass spectrometric analysis of the contents of the stored second output stream.

2. The method of claim 1, further comprising the steps of:
    g) detecting a characteristic of the first output stream; and
    h) controlling step e) responsive to step g).

3. The method of claim 1 wherein step h) includes varying a flow rate of any of the stored first output stream and the stored second output stream into a mass spectrometer.

4. The method of claim 1, further comprising the step of:
    g) collecting at least one discrete fraction of the first output stream.

5. The method of claim 4, further comprising the steps of:
    h) detecting a characteristic of the first output stream; and
    i) controlling step g) responsive to step h).

6. A system for analyzing a first sample and a second sample, the system comprising comprising:
    a first separation column adapted to separate the first sample to generate a species segment of a first output stream;
    a second separation column adapted to separate the second sample to generate a species segment of a second output stream;
    a first microfluidic storage line in fluid communication with the first separation column, wherein the first microfluidic storage line has a volume sufficient to store substantially all of the species segment of the first output stream;
    a second microfluidic storage line in fluid communication with the second separation column, wherein the second microfluidic storage line has a volume sufficient to store substantially all of the species segment of the second output stream; and
    a mass spectrometer in selective fluid communication with the first storage line and the second storage line.

7. The system of claim 6 further comprising a detector adapted to detect at least one characteristic of the first output stream.

8. The system of claim 7, further comprising:
    a fraction collector capable of fluid communication with the first separation column; and
    a valve interposed between the fraction collector and the first separation column;
    wherein operation of the valve is responsive to the detector.

9. The system of claim 6, further comprising:
    a translation stage positioned proximate to and in fluid communication with the mass spectrometer;
    a first electrospray needle affixed to the translation stage and in fluid communication with the first microfluidic storage line; and
    a second electrospray needle affixed to the translation stage and in fluid communication with the second microfluidic storage line.

10. The system of claim 6, further comprising:
    an electrospray needle positioned proximate to and in fluid communication with the mass spectrometer; and
    a multi-port switching valve in fluid communication with the electrospray needle, the first microfluidic storage line, and the second microfluidic storage line.

* * * * *